United States Patent
Fujita et al.

(10) Patent No.: US 8,871,873 B2
(45) Date of Patent: Oct. 28, 2014

(54) BIODEGRADABLE PARTICLE, VASCULAR EMBOLIZATION MATERIAL AND METHOD FOR PRODUCING BIODEGRADABLE PARTICLES

(75) Inventors: Masaki Fujita, Otsu (JP); Megumi Nakanishi, Otsu (JP); Yoshitake Takahashi, Otsu (JP); Yasufumi Yamamura, Otsu (JP); Kazuhiro Tanahashi, Otsu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/008,194

(22) PCT Filed: Mar. 29, 2012

(86) PCT No.: PCT/JP2012/058293
§ 371 (c)(1),
(2), (4) Date: Sep. 27, 2013

(87) PCT Pub. No.: WO2012/133608
PCT Pub. Date: Oct. 4, 2012

(65) Prior Publication Data
US 2014/0018505 A1 Jan. 16, 2014

(30) Foreign Application Priority Data
Mar. 30, 2011 (JP) ................................. 2011-076155

(51) Int. Cl.
| | | |
|---|---|---|
| A61L 24/04 | (2006.01) | |
| A61L 24/00 | (2006.01) | |
| C08J 3/28 | (2006.01) | |
| C08G 63/664 | (2006.01) | |
| C08G 63/08 | (2006.01) | |
| A61L 31/06 | (2006.01) | |
| A61L 31/14 | (2006.01) | |
| C08G 65/32 | (2006.01) | |

(52) U.S. Cl.
CPC ............ *A61L 24/046* (2013.01); *A61L 24/0042* (2013.01); *A61L 2430/36* (2013.01); *C08J 3/28* (2013.01); *C08J 2367/04* (2013.01); *C08G 63/664* (2013.01); *C08G 63/08* (2013.01); *A61L 31/06* (2013.01); *A61L 31/148* (2013.01)
USPC ........................................................ 525/411

(58) Field of Classification Search
USPC ........................................................ 525/411
See application file for complete search history.

(56) References Cited

U.S. PATENT DOCUMENTS

| | | |
|---|---|---|
| 4,526,938 A | 7/1985 | Churchill et al. |
| 5,202,352 A | 4/1993 | Okada et al. |
| 2006/0069168 A1 | 3/2006 | Tabata et al. |
| 2007/0003592 A1 | 1/2007 | Hissink |
| 2009/0117033 A1 | 5/2009 | O'Gara |
| 2009/0311337 A1 | 12/2009 | Tanahashi et al. |

FOREIGN PATENT DOCUMENTS

| | | |
|---|---|---|
| JP | 5-969 | 1/1993 |
| JP | 05-017245 | 1/1993 |
| JP | 2004-167229 | 6/2004 |
| JP | 2005-312623 | 11/2005 |
| JP | 2005-314535 | 11/2005 |
| JP | 2005-533148 | 11/2005 |
| JP | 2007-145826 | 6/2007 |
| JP | 2007-146146 | 6/2007 |
| JP | 2007-291323 | 11/2007 |

*Primary Examiner* — Terressa Boykin
(74) *Attorney, Agent, or Firm* — DLA Piper LLP (US)

(57) ABSTRACT

A biodegradable particle including a block copolymer produced by copolymerization of a biodegradable copolymer having a structure composed of hydroxycarboxylic acid a1, whose homopolymer produced by homopolymerization has a glass transition point of not less than 40° C., and hydroxycarboxylic acid a2, whose homopolymer produced by homopolymerization has a glass transition point of not more than −40° C.; a water-soluble polymer comprising a functional group selected from the group consisting of a hydroxyl group, amino group and carboxylic acid group at each of both ends; and a polyvalent compound comprising 2 or more functional groups each selected from the group consisting of a hydroxyl group, amino group and carboxylic acid group; wherein a ratio of mass of said structure composed of hydroxycarboxylic acid a2 to mass of said biodegradable copolymer is 30 to 90% by mass.

9 Claims, No Drawings

BIODEGRADABLE PARTICLE, VASCULAR EMBOLIZATION MATERIAL AND METHOD FOR PRODUCING BIODEGRADABLE PARTICLES

TECHNICAL FIELD

This disclosure relates to a biodegradable particle, vascular embolization material, and a method of producing a biodegradable particle.

BACKGROUND

For the purposes of hemostasis upon incision of an affected area, blocking of the nutrient supply to a tumor, maintenance of the concentration of an anticancer drug in a tumor, and the like, a poly(lactic acid/glycolic acid) copolymer (JP 5-969 A), a block copolymer of polyethylene glycol and polylactic acid (JP 5-17245 B, JP 2004-167229 A, JP 2005-312623 A and JP 2007-291323 A), or a multiblock copolymer obtained by copolymerizing lactic acid, polyethylene glycol, polyvalent carboxylic acid and the like (US Publication No. 2009/0117033) is used as polymer particles for embolization of blood vessels and the like.

Such polymer particles for embolization of blood vessels and the like are used in the shape of spherical particles to tightly and securely embolize the blood vessels and the like. However, since the particles are delivered to the target site such as a blood vessel through a microcatheter or the like, the particles have problems such as insufficient flexibility of the particles themselves, occurrence of aggregation to cause clogging of the catheter, and irreversible deformation of the polymer particles before they reach the target site.

To solve these problems, attempts have been made, for example, by covering the surface of the polymer particles with polyethylene glycol to prevent their aggregation and hence to increase their ability to pass through a catheter (JP 2007-145826 A), by blending a plurality of types of polymers to control flexibility of the polymer particles (JP 2007-146146 A), or by developing a chemically cross-linked polymer particle (JP 2005-314535 A).

However, although an increase in the ability to pass through a catheter and improvement in controlling flexibility of the polymer particles can be seen in the improved techniques such as covering of the surface of polymer particles (JP 2007-145826 A), blending of a plurality of types of polymers (JP 2007-146146 A) and use of chemically cross-linked polymer particles (JP 2005-314535 A), insufficient improvement can be seen in terms of the problem of irreversible deformation of polymer particles. Hence, further improvement has been required to obtain a good embolization action for blood vessels and the like. That is, development of an embolization material for blood vessels and the like wherein the ability of the polymer particles to recover their original shape after passing through a catheter (hereinafter referred to as "particle shape-recovering ability") is enhanced has been demanded.

In view of this, it could be helpful to provide a biodegradable vascular embolization material that is less likely to coagulate and has an improved flexibility, and whose particle shape is recovered after its passing through a catheter or the like.

SUMMARY

We thus provide the biodegradable particle, vascular embolization material, and methods of producing them described in (1) to (9) below.

(1) A biodegradable particle comprising a block copolymer produced by copolymerization of: a biodegradable copolymer having a structure composed of at least hydroxycarboxylic acid a1 and hydroxycarboxylic acid a2; a water-soluble polymer comprising a functional group selected from the group consisting of a hydroxyl group, amino group and carboxylic acid group at each of both ends; and a polyvalent compound comprising 2 or more functional groups each selected from the group consisting of a hydroxyl group, amino group and carboxylic acid group; wherein a homopolymer produced by homopolymerization of the hydroxycarboxylic acid a1 has a glass transition point of not less than 40° C., a homopolymer produced by homopolymerization of the hydroxycarboxylic acid a2 has a glass transition point of not more than −40° C., and the weight ratio of the structure composed of hydroxycarboxylic acid a2 in the biodegradable copolymer is 30 to 90% by weight.

(2) The biodegradable particle according to (1), wherein the block copolymer is a multiblock copolymer comprising a repetitive unit represented by Formula (I) below:

wherein A represents a block composed of the biodegradable copolymer or a copolymer produced by covalent bonding of 2 or more of the biodegradable copolymer; B represents a block composed of the water-soluble polymer; C represents a single bond or a structure composed of the polyvalent compound; and n represents an integer of 1 or more.

(3) The biodegradable particle according to (1) or (2), wherein the 40% compression load in the water-saturated state is not more than 500 mN, and, when the compression rate in the water-saturated state is 10%, the compression recovery rate is not less than 40%.

(4) The biodegradable particle according to any one of (1) to (3), wherein the weight average molecular weight of the block copolymer is 3000 to 300000.

(5) The biodegradable particle according to any one of (1) to (4), wherein the weight average molecular weight of the water-soluble polymer is 200 to 50000.

(6) The biodegradable particle according to any one of (1) to (5), wherein the hydroxycarboxylic acid a1 is lactic acid.

(7) The biodegradable particle according to any one of (1) to (6), wherein the hydroxycarboxylic acid a2 is 6-hydroxycaproic acid.

(8) A vascular embolization material composed of the biodegradable particle according to any one of (1) to (7).

(9) A method of producing a sterilized biodegradable particle, the method comprising:
a copolymerization step of copolymerizing:
a biodegradable copolymer having a structure composed of at least hydroxycarboxylic acid a1 and hydroxycarboxylic acid a2, wherein a homopolymer produced by homopolymerization of the hydroxycarboxylic acid a1 has a glass transition point of not less than 40° C., a homopolymer produced by homopolymerization of the hydroxycarboxylic acid a2 has a glass transition point of not more than −40° C., and the weight ratio of the structure composed of hydroxycarboxylic acid a2 in the biodegradable copolymer is 30 to 90% by weight;
a water-soluble polymer comprising a functional group selected from the group consisting of a hydroxyl group, amino group and carboxylic acid group at each of both ends; and a polyvalent compound comprising 2 or more functional groups each selected from the group consisting of a hydroxyl group, amino group and carboxylic acid to obtain a block copolymer;

a granulation step of granulating the block copolymer to obtain a biodegradable particle; and a radiation irradiation step of irradiating the biodegradable particle with radiation to obtain a sterilized biodegradable particle.

The biodegradable particles can be suitably used as a vascular embolization material since aggregation of the particles is less likely to occur and the particles can be easily delivered to the target site such as a blood vessel without causing clogging inside a catheter or the like. Further, since the biodegradable particles have an enhanced particle shape-recovering ability after passing through a catheter or the like, the target site can be effectively embolized using a minimum necessary amount of the particles.

DETAILED DESCRIPTION

The terms used herein are as defined below unless otherwise specified.

The biodegradable particle comprises a block copolymer produced by copolymerization of: a biodegradable copolymer having a structure composed of at least hydroxycarboxylic acid a1 and hydroxycarboxylic acid a2; a water-soluble polymer comprising a functional group selected from the group consisting of a hydroxyl group, amino group and carboxylic acid group at each of both ends; and a polyvalent compound comprising 2 or more functional groups each selected from the group consisting of a hydroxyl group, amino group and carboxylic acid group; wherein a homopolymer produced by homopolymerization of the hydroxycarboxylic acid a1 has a glass transition point of not less than 40° C., a homopolymer produced by homopolymerization of the hydroxycarboxylic acid a2 has a glass transition point of not more than −40° C., and the weight ratio of the structure composed of hydroxycarboxylic acid a2 in the biodegradable copolymer is 30 to 90% by weight.

The term "biodegradability" means the property of the particle composed of a specific block copolymer or the biodegradable copolymer to be degraded, dissolved, absorbed or metabolized in the living body, or the property of the particle or copolymer to be excreted from the body to the outside thereof.

The "hydroxycarboxylic acid" includes acid halides of hydroxycarboxylic acids, acid anhydrides of hydroxycarboxylic acids, esters of hydroxycarboxylic acids, and cyclic compounds such as cyclic dimers of hydroxycarboxylic acids. Further, in terms of a hydroxycarboxylic acid having optical isomers such as malic acid or tartaric acid, the hydroxycarboxylic acid includes all of its D-isomer and L-isomer, and their mixtures. Further, the hydroxycarboxylic acid includes copolymers produced by copolymerization of these hydroxycarboxylic acids. Examples of the hydroxycarboxylic acid include glycolic acid, lactic acid, glyceric acid, hydroxybutyric acid, malic acid, tartaric acid, hydroxyvaleric acid, 3-hydroxyhexanoic acid and 6-hydroxycaproic acid. Examples of the cyclic compound composed of hydroxycarboxylic acid include glycolide, which is the cyclic dimer of glycolic acid, lactide, which is the cyclic dimer of lactic acid, and ε-caprolactone, which corresponds to 6-hydroxycaproic acid. Examples of the copolymer produced by copolymerization of hydroxycarboxylic acids include copolymers of lactic acid and glycolic acid, and copolymers of 6-hydroxycaproic acid and glycolic acid. Among these, examples of the "hydroxycarboxylic acid a1" whose homopolymer produced by homopolymerization has a glass transition point of not less than 40° C. include lactic acid, copolymers of lactic acid and glycolic acid, copolymers of lactic acid and terephthalic acid, and copolymers of lactic acid and isophthalic acid; and examples of the "hydroxycarboxylic acid a2" whose homopolymer produced by homopolymerization has a glass transition point of not more than −40° C. include 6-hydroxycaproic acid, copolymers of 6-hydroxycaproic acid and glycolic acid, and copolymers of 6-hydroxycaproic acid and polybutylene succinate (a copolymer of 1,4-butanediol and succinic acid). In particular, hydroxycarboxylic acid a1 is preferably lactic acid, and hydroxycarboxylic acid a2 is preferably 6-hydroxycaproic acid. The "homopolymer" means a polymer produced by polymerization of a single type of monomers such as polylactic acid, which is produced by polymerization of lactic acid alone, but the "homopolymer produced by homopolymerization" in the present invention also includes polymers produced by polymerization of a single type of copolymers such as copolymers of lactic acid and glycolic acid.

Although a macromolecular compound with a high glass transition point has low mobility of the polymer molecular chain due to its solidity, high rigidity and low fluidity, the homopolymer produced by homopolymerization of hydroxycarboxylic acid a1 has a glass transition point of preferably not less than 50° C., more preferably not less than 55° C. The homopolymer produced by homopolymerization of hydroxycarboxylic acid a2 has a glass transition point of preferably not more than −50° C., more preferably not more than −55° C.

The "biodegradable copolymer" means a copolymer having biodegradability. The copolymer herein means a macromolecular compound obtained by copolymerization of 2 or more types of monomers, that is a copolymerized product having a structure composed of 2 or more types of monomers. The biodegradable copolymer needs to have a structure composed of at least hydroxycarboxylic acid a1 and hydroxycarboxylic acid a2, that is, to comprise hydroxycarboxylic acid a1 and hydroxycarboxylic acid a2 as raw material monomers, but the biodegradable copolymer may have a structure composed of monomers (hereinafter referred to as "monomer a3") other than hydroxycarboxylic acid a1 or hydroxycarboxylic acid a2. Examples of the compound that corresponds to monomer a3 include diols such as glycolic acid or glycolide, ethylene glycol, propylene glycol, trimethylene glycol, diethylene glycol and 1,4-butanediol; dicarboxylic acids such as oxalic acid, malonic acid, succinic acid, glutaric acid, adipic acid, pimelic acid, suberic acid, azelaic acid, sebacic acid, malic acid, tartaric acid and dodecanedioic acid; and their acid halides, acid anhydrides and esters. Glycolic acid or glycolide, or polybutylene succinate is preferred as the monomers.

Each of hydroxycarboxylic acid a1 and hydroxycarboxylic acid a2 may be a mixture of 2 or more types of hydroxycarboxylic acids. Monomer a3 may also be a mixture of 2 or more types of compounds.

The weight ratio of the structure composed of hydroxycarboxylic acid a2 in the biodegradable copolymer needs to be 30 to 90% by weight, and, for achieving appropriate flexibility of the obtained biodegradable particle, the weight ratio is preferably 50 to 85% by weight, more preferably 70 to 80% by weight.

In cases where monomer a3 is glycolic acid or glycolide, the weight ratio of the structure composed of monomer a3 in the biodegradable copolymer is preferably not less than 5% by weight, preferably not less than 10% by weight, for further increasing the biodegradability. On the other hand, the weight ratio is preferably not more than 35% by weight, more preferably not more than 30% by weight, for avoiding a decrease in the solubility in an organic solvent.

In cases where the weight average molecular weight of the biodegradable copolymer is too small, the obtained biodegradable particle is gelled and adheres to the inside of a catheter. On the other hand, in cases where the weight average molecular weight is too large, biodegradability of the obtained biodegradable particle is low. Therefore, the weight average molecular weight of the biodegradable copolymer is preferably 200 to 100000, more preferably 1000 to 80000. The weight average molecular weight of the biodegradable copolymer can be measured by gel permeation chromatography (hereinafter referred to as "GPC method") under the following conditions.

[Measurement Conditions]

Apparatus (column): TSK gel $GMH_{HR}$-M (manufactured by Toso Corporation; inner diameter, 7.8 mm; length, 30 cm; two columns are linearly arranged)

Eluent: Chloroform
Column temperature: 35° C.
Flow rate: 1.0 mL/min.
Detection method: Refractive index
Calibration curve: Prepared using polystyrene standard samples Examples of the "water-soluble polymer comprising a functional group selected from the group consisting of a hydroxyl group, amino group and carboxylic acid group at each of both ends" include polyalkylene glycols such as polyethylene glycol (hereinafter referred to as "PEG") and polypropylene glycol, and their derivatives; and copolymers of alkylene glycol and an excess amount of dicarboxylic acid. Water-soluble polymers having a hydroxyl group at both ends are preferred and, because of its high biocompatibility and biodegradability, PEG is more preferred. The carboxylic acid group may be converted to an acid halide structure, ester structure or acid anhydride structure.

In cases where the weight average molecular weight of the water-soluble polymer is too small, hydrophilicity of the obtained biodegradable particle is low, and hence uniform biodegradability cannot be obtained. On the other hand, in cases where the weight average molecular weight is too large, excretion of the water-soluble polymer as a decomposition product of the obtained biodegradable particle to the outside of the body is difficult. Therefore, the weight average molecular weight of the water-soluble polymer is preferably 200 to 50000, more preferably 1000 to 40000. The weight average molecular weight of the water-soluble polymer can be measured by the GPC method.

Examples of the "polyvalent compound comprising 2 or more functional groups each selected from the group consisting of a hydroxyl group, amino group and carboxylic acid group" include dicarboxylic acids such as oxalic acid, malonic acid, succinic acid, glutaric acid, adipic acid, pimelic acid, suberic acid, azelaic acid, sebacic acid, malic acid, tartaric acid and dodecanedioic acid; citric acid; and multibranched polymers such as hyperbranched polymers and dendrimers; which have 2 or more functional groups each selected from the group consisting of a hydroxyl group, amino group and carboxylic acid group at the ends of branches; and their acid halides, acid anhydrides and esters. That is, the carboxylic acid group may be converted to an acid halide structure, ester structure or acid anhydride structure.

The "block copolymer" means a copolymer having a molecular structure wherein 2 or more types of polymers having different properties are linked together via a covalent bond(s) to form a long chain, and the block means each of the "2 or more types of polymers having different properties" constituting the block copolymer. The block copolymer is formed by copolymerization of the biodegradable copolymer, water-soluble polymer and polyvalent compound described above, and is preferably a multiblock copolymer having a repetitive unit represented by Formula (I) below:

$$\pm B\text{---}C\text{---}A\pm_n \qquad (I)$$

wherein A represents a block composed of the biodegradable copolymer or a copolymer produced by covalent bonding of 2 or more of the biodegradable copolymer; B represents a block composed of the water-soluble polymer; C represents a single bond or a structure composed of the polyvalent compound; and n represents an integer of 1 or more.

A covalent bond may be formed between a terminal hydroxyl group or amino group of the water-soluble polymer and a carboxylic acid group of the polyvalent compound. Further, a covalent bond may be formed between a terminal carboxylic acid group of the water-soluble polymer and a hydroxyl group or amino group of the polyvalent compound. The carboxylic acid group of each of them may be converted to an acid halide structure, ester structure or acid anhydride structure.

Value X, which is calculated according to the Equation (1) below from: Nb, which is the number of moles of the water-soluble polymer; m, which is the number of hydroxyl groups, amino groups and carboxylic acid groups in the polyvalent compound; and Nc, which is the number of moles of the polyvalent compound; is preferably 0.8 to 1.2, more preferably 0.9 to 1.1.

$$X = (2 \times Nb)/(m \times Nc) \qquad (1)$$

In this equation, Nb and Nc are calculated according to the Equations (2) and (3) below, respectively.

$$Nb = Wb/Mwb \qquad (2)$$

Wb: weight (g) of the water-soluble polymer used in the copolymerization

Mwb: weight average molecular weight (g/mol) of the water-soluble polymer used in the copolymerization $$Nc = Wc/Mwc \qquad (3)$$

Wc: weight (g) of the polyvalent compound used in the copolymerization

Mwc: molecular weight (g/mol) of the polyvalent compound used in the copolymerization In cases where the weight average molecular weight of the block copolymer is too small, the obtained biodegradable particle is gelled and adheres to the inside of a catheter. On the other hand, in cases where the weight average molecular weight is too large, biodegradability of the obtained biodegradable particle is low. Therefore, the weight average molecular weight of the block copolymer is preferably 3000 to 300000, more preferably 4000 to 200000. The weight average molecular weight of the block copolymer can be measured by the GPC method.

For achieving an appropriate solubility in water or an organic solvent, the weight ratio of block A to block B in the multiblock copolymer is preferably 100 to 600% by weight, more preferably 150 to 550% by weight, still more preferably 200 to 500% by weight.

The weight ratio of a specific structure in the biodegradable copolymer, the weight ratio of block A to block 13 in the multiblock copolymer, and the like can be calculated based on the result of measurement by proton nuclear magnetic resonance spectroscopy (hereinafter referred to as "$^1$H-NMR") under the following conditions. For example, in cases where hydroxycarboxylic acid a1 is lactic acid, the hydrogen atom at the α-position which is a methine group is characteristic (chemical shift value, about 5.2 ppm). In cases where hydroxycarboxylic acid a2 is 6-hydroxycaproic acid, the hydrogen atom at the α-position which is a methylene group is characteristic (chemical shift value, about 2.3 ppm). In cases where monomer a3 is glycolic acid, the hydrogen atom at the α-position which is a methylene group is characteristic (chemical shift value, about 4.8 ppm). Further, in cases where the water-soluble polymer is PEG, the 4 hydrogen atoms at the ethylene group are characteristic (chemical shift value, about 3.5 ppm). Based on the integrated value of the signal that appears at the chemical shift for each of these characteristic hydrogen atoms, each weight ratio can be calculated.

[Measurement Conditions]

Apparatus: JNM-EX270 (manufactured by JEOL, 270 MHz)

Solvent: Deuterated chloroform (containing 0.05% by volume TMS as an internal standard)

Measurement temperature: 20° C.

In the biodegradable particle, the 40% compression load in the water-saturated state is not more than 500 mN, and, when the compression rate in the water-saturated state is 10%, the compression recovery rate is not less than 40%.

The "water-saturated state" means a state where, when about 20 mg of the biodegradable particle is immersed in 10 mL of phosphate buffered saline at 37° C. (while a test tube as a container is rotated using a rotator at a rate of 0.5 rotation/second to stir the content of the tube), the water content of the biodegradable particle is constant. "Constant water content" herein means a state where, when the weight of the biodegradable particle immersed in phosphate buffered saline at 37° C. is measured every minute, the rate of its change with time is not more than 10%. The rate of change with time is the value Rw (%) which can be calculated according to Equation (4) below.

$$Rw = \{W(t) - W(t-1)\}/W(t) \times 100 \quad (4)$$

W(t): weight (g) of the biodegradable particle after immersion in water for t minutes W(t−1): weight (g) of the biodegradable particle after immersion in water for (t−1) minutes The "40% compression load" is an index representing flexibility of a biodegradable particle, and means the load required for compressing a single biodegradable particle to 40% of the diameter of the original particle. In cases where the 40% compression load is too small, the shape of the biodegradable particle cannot be maintained, while in cases where the 40% compression load is too large, resistance upon passing through a catheter or the like is high, so that the 40% compression load of the biodegradable particle in the water-saturated state is preferably 5 to 500 mN, more preferably 10 to 450 mN.

The 40% compression load of the biodegradable particle can be measured using a micro compression tester under the following conditions. More specifically, a load is applied to the particle to the following set test force to measure the load required for compressing the particle to 40% of the particle diameter of the original particle.

[Measurement Conditions]

Test name: Compression test

Apparatus: MCT-510 (manufactured by Shimadzu Corporation)

Set test force: 4903 mN

Load rate: 207 mN/s

Load retention time: 0 s

Upper pressurization factor: Plane, 500 μm (diameter)

The "compression recovery rate" means the ability of the biodegradable particle to recover, after passing through a catheter having a small inner diameter or the like and becoming free from compression, its original particle shape that was retained before the compression. That is, the compression recovery rate means an index representing the particle shape-recovering ability. In cases where the compression recovery rate is too small, the biodegradable particle passes the target site of the blood vessel which should be embolized and flows downstream. Therefore, the compression recovery rate of the biodegradable particle at a compression rate of 10% in the water-saturated state is preferably not less than 40%, more preferably not less than 50%.

The compression recovery rate of the biodegradable particle at a compression rate of 10% in the water-saturated state is similarly measured using a micro compression tester under the following conditions, and corresponds to the value Rr (%) calculated according to the Equations (5) to (7) below. More specifically, a load is applied to each particle to the set test force obtained in the compression test at a compression rate of 10% (that is, maximum test force), and the load is then removed to the minimum test force.

[Measurement Conditions]

Test name: Load/load removal test

Apparatus: MCT-510 (manufactured by Shimadzu Corporation)

Set test force: Test force obtained in the compression test when the compression rate of each particle is 10%

Load rate: 4.5 mN/s

Load retention time: 2 s

Upper pressurization factor:

Plane diameter, 500 μm (diameter)

$$L1 = L1_b - L1_a \quad (5)$$

$L1_a$: Particle diameter change (μm) upon loading of the minimum test force $L1_b$: Particle diameter change (μn) upon loading of the maximum test force $$L2 = L2_b - L1_a \quad (6)$$

L2b: Particle diameter change (μm) upon loading of the maximum test force followed by removal of the load to the minimum test force $$Rr = \{(L1 - L2)/L1\} \times 100 \quad (7)$$

The "compression rate" means the ratio of the particle diameter after compression of the biodegradable particle to its original particle diameter, and corresponds to the value Cr (%) calculated according to Equation (8) below.

$$Cr = (L1/d) \times 100 \quad (8)$$

d: Average particle diameter (μm) of the biodegradable particle

In consideration of the diameter of the blood vessel at the main target site of embolization, the average particle diameter of the biodegradable particle is preferably 5 to 2000 μm, more preferably 10 to 1500 μm. The particle diameter of the medical biodegradable particle can be measured by the light scattering method.

The vascular embolization material is composed of the biodegradable particle.

In cases where the biodegradable particle is used as a vascular embolization material, the biodegradable particle may be used as it is, or may be used as a dispersion in a contrast medium or dispersion medium. Examples of the contrast medium herein include water-soluble contrast media such as iopamidol injection, ioxaglic acid injection and iohexyl injection; and oily contrast media such as iodized poppy oil. Water-soluble contrast media are preferred. Examples of the dispersion medium include aqueous injection solutions and vegetable oils such as sesame oil and corn oil, containing a dispersant such as a polyoxysorbitan fatty acid ester, preservative such as methylparaben, or isotonic agent such as sodium chloride. The vascular embolization material may also contain an antiseptic, stabilizer, solubilizer, vehicle, and/or an effective component such as an antitumor agent.

The method of producing a sterilized biodegradable particle comprises: a copolymerization step of copolymerizing the biodegradable copolymer, the water-soluble polymer and the polyvalent compound to obtain the block copolymer; a granulation step of granulating the block copolymer to obtain a biodegradable particle; and a radiation irradiation step of irradiating the biodegradable particle with radiation to obtain a sterilized biodegradable particle.

The "copolymerization step" is a step to obtain a block copolymer by copolymerizing the biodegradable copolymer, the water-soluble polymer and the polyvalent compound. To control the weight ratio and the like of each specific structure in the biodegradable copolymer appropriately, it is preferred to preliminarily obtain the biodegradable copolymer and then to copolymerize the obtained biodegradable copolymer with the water-soluble polymer and the polyvalent compound. Alternatively, a mixture of: hydroxycarboxylic acid a1 and hydroxycarboxylic acid a2 (and, as required, monomer a3); and the water-soluble polymer and the polyvalent compound; may be subjected at once to copolymerization. Alternatively, only hydroxycarboxylic acid a1 and hydroxycarboxylic acid a2 may be preliminarily copolymerized, followed by adding monomer a3 when copolymerization with the water-soluble polymer and the polyvalent compound is carried out.

In cases where hydroxycarboxylic acid a1, hydroxycarboxylic acid a2 and monomer a3 are lactic acid, 6-hydroxycaproic acid and glycolic acid or the like, respectively, the copolymerization reaction in the copolymerization step is preferably condensation polymerization. On the other hand, in cases where hydroxycarboxylic acid a1, hydroxycarboxylic acid a2 and monomer a3 are cyclic compounds, for example, lactide, $\epsilon$-caprolactone and glycolide, respectively, ring-opening polymerization is preferred.

In cases where the biodegradable copolymer is obtained preliminarily, the reaction solvent is a good solvent for hydroxycarboxylic acid a1 and hydroxycarboxylic acid a2 (and, as required, monomer a3). Examples of the good solvent include dichloromethane, chloroform and tetrahydrofuran, and mixed solvents thereof. The reaction temperature is set such that the good solvent refluxes. The reaction pressure may be a reduced pressure, but, for simplicity of the operation, normal pressure is preferred. The reaction time is preferably 2 to 24 hours, more preferably 4 to 20 hours for appropriately controlling the molecular weight of the obtained biodegradable copolymer.

On the other hand, in cases where hydroxycarboxylic acid a1, hydroxycarboxylic acid a2 and monomer a3 are cyclic compounds, for example, lactide, $\epsilon$-caprolactone and glycolide, respectively, that is, in cases where the copolymerization reaction is ring-opening polymerization, it is preferred to use no reaction solvent and to set the reaction temperature to 100 to 180° C., more preferably 110 to 160° C., for increasing reactivity.

In cases where the biodegradable copolymer is preliminarily obtained, the total concentration of hydroxycarboxylic acid a1 and hydroxycarboxylic acid a2 (and, as required, monomer a3) is preferably 10 to 100% by weight, more preferably 50 to 100% by weight, although the total concentration varies depending on the type of the hydroxycarboxylic acids and the like. In terms of the catalyst concentration in the reaction solvent, if the concentration is too high, removal of the catalyst after the reaction is difficult, while if the concentration is too low, the reaction hardly proceeds, so that the catalyst concentration is preferably 0.01 to 0.5% by weight, more preferably 0.1 to 0.3% by weight.

The preliminarily obtained biodegradable copolymer may be once purified, but it is also possible to subject the biodegradable copolymer without purification to an additional copolymerization reaction for obtaining a block copolymer.

As the reaction solvent for the copolymerization reaction by condensation polymerization of the preliminarily obtained biodegradable copolymer with the water-soluble polymer and the polyvalent compound (and, as required, monomer a3), a good solvent for the biodegradable copolymer, water-soluble polymer and polyvalent compound (and, as required, monomer a3) is used. Examples of such a good solvent include dichloromethane, chloroform and tetrahydrofuran, and mixed solvents thereof. The reaction temperature and the reaction pressure are set such that the good solvent refluxes. As the good solvent, diphenyl ether, which has a high boiling point, is also preferably used. In cases where diphenyl ether is used, the reaction temperature is preferably 150 to 200° C., more preferably 160 to 190° C. for allowing the reaction to proceed appropriately while removing water as a by-product and avoiding evaporation of the diphenyl ether itself. By the same reason, the reaction pressure is preferably 1 to 5 kPa, more preferably 2 to 4 kPa. The reaction time is preferably 10 to 30 hours, more preferably 15 to 25 hours to appropriately control the molecular weight of the obtained biodegradable copolymer. Although the copolymerization reaction may be carried out under air atmosphere, the reaction is carried out preferably under an atmosphere of inert gas such as argon, helium or nitrogen, more preferably under an atmosphere of nitrogen, which is inexpensive.

In the copolymerization reaction of the preliminarily obtained biodegradable copolymer with the water-soluble polymer and the polyvalent compound (and, as required, monomer a3), the total concentration of the biodegradable copolymer, water-soluble polymer and polyvalent compound (and, as required, monomer a3) is preferably 30 to 70% by weight, more preferably 40 to 60% by weight to appropriately control the copolymerization reaction. In terms of the catalyst concentration in the reaction solvent, if the concentration is too high, removal of the catalyst after the reaction is difficult, while if the concentration is too low, the reaction hardly proceeds, so that the catalyst concentration is preferably 0.01 to 0.5 weight, more preferably 0.1 to 0.3 weight.

Examples of the catalyst include metal catalysts. Examples of the metal catalysts include metal alkoxides, metal halides, organic carboxylic acid salts, carbonic acid salts, sulfuric acid salts and oxides of tin, titanium, lead, zinc, cobalt, iron, lithium or a rare earth. In view of polymerization reactivity, tin compounds are preferred. Examples of the tin compounds include tin powder, tin(II) chloride, tin(IV) chloride, tin(II) bromide, tin(IV) bromide, ethoxytin(II), t-butoxytin(IV), isopropoxytin(IV), tin(II) acetate, tin(IV) acetate, tin(II) octylate, tin(II) laurate, tin(II) myristate, tin(II) palmitate, tin(II) stearate, tin(II) oleate, tin(II) linoleate, tin(II) acetylacetonate, tin(II) oxalate, tin(III) lactate, tin(II) tartrate, tin(II) pyrophosphate, tin(II) p-phenolsulfonate, tin(II) bis(methanesulfonate), tin(II) sulfate, tin(II) oxide, tin(IV) oxide, tin (II) sulfide, tin(IV) sulfide, dimethyltin(IV) oxide, methylphenyltin(IV) oxide, dibutyltin(IV) oxide, dioctyltin(IV) oxide, diphenyltin(IV) oxide, tributyltin oxide, triethyltin (IV) hydroxide, triphenyltin(IV) hydroxide, tributyltin hydride, monobutyltin(IV) oxide, tetramethyltin(IV), tetraethyltin(IV), tetrabutyltin(IV), dibutyldiphenyltin(IV), tetraphenyltin(IV), tributyltin(IV) acetate, triisobutyltin(IV) acetate, triphenyltin(IV) acetate, dibutyltin diacetate, dibutyltin dioctoate, dibutyltin(IV) dilaurate, dibutyltin(IV) maleate, dibutyltin bis(acetylacetonate), tributyltin(IV) chloride, dibutyltin dichloride, monobutyltin trichloride, dioctyltin dichloride, triphenyltin(IV) chloride, tributyltin sulfide, tributyltin sulfate, tin(II) methanesulfonate, tin(II) ethanesulfonate, tin(II) trifluoromethanesulfonate, ammonium hexachlorostannate(IV), dibutyltin sulfide, diphenyltin sulfide, triethyltin sulfate and tin(II) phthalocyanine. The catalyst in the ring-opening polymerization is preferably tin(II) octylate, and the catalyst in the condensation polymerization is preferably tin(II) oxide.

Although the block copolymer obtained in the copolymerization step may be subjected to the granulation step without purification, purification may be carried out to remove unreacted compounds, the solvent and the catalyst. Examples of the method of such purification include fractional precipitation. The fractional precipitation is a method wherein the obtained block polymer is dissolved in a good solvent and the resulting solution is added dropwise to a stirred poor solvent, to obtain a purified block copolymer as a precipitate. The "good solvent" herein means an organic solvent wherein both of the biodegradable copolymer and the water-soluble polymer can be dissolved, and the "poor solvent" means an organic solvent wherein either one of the biodegradable polymer and the soluble polymer cannot be dissolved.

Examples of the good solvent used in the fractional precipitation include dichloromethane, chloroform and tetrahydrofuran, and mixed solvents thereof. The amount of the good solvent varies depending on the composition of the obtained block copolymer and the like, and the concentration of the dissolved block copolymer is preferably 1 to 50% by weight, more preferably 10 to 40% by weight. Examples of the poor solvent used in the fractional precipitation include alcohol-based organic solvents such as methanol and ethanol; ether-based organic solvents such as dimethyl ether, ethyl methyl ether and diethyl ether; hydrocarbon-based organic solvents such as pentane, hexane, heptane and octane; and mixed solvents thereof. The amount of the poor solvent again varies depending on the composition of the obtained block copolymer and the like, and is preferably 2 to 100% by weight, more preferably 5 to 50% by weight with respect to the good solvent. More specifically, a method wherein the block copolymer obtained in the copolymerization step is dissolved in chloroform and the resulting solution is added dropwise to stirred diethyl ether/hexane=1/1 (weight ratio) is preferred in view of controlling the molecular weight distribution.

The "granulation step" is a step wherein the block copolymer obtained in the copolymerization step is granulated to obtain a biodegradable particle. Examples of the granulation method in the granulation step include tumbling granulation, fluidized bed granulation, spray bed granulation, mixing granulation, disintegration granulation, compression granulation, extrusion granulation and droplet solidification granulation. To effectively control the particle shape, particle diameter and the like, droplet solidification granulation is preferred. In particular, a known oil/water type (hereinafter referred to as "O/W-type") drying-in-liquid method or water/oil/water-type drying-in-liquid method, in which the block copolymer obtained in the copolymerization step is dissolved in an organic solvent that is not compatible with water and then dispersed in a stirred aqueous layer (containing an emulsifier), is more preferred.

Examples of the organic solvent that is not compatible with water include dichloromethane, chloroform, ethyl acetate and isopropyl ether, and mixed solvents thereof. Examples of the emulsifier include anionic surfactants such as sodium oleate, sodium stearate and sodium laurate; nonionic surfactants such as polyoxyethylene sorbitan fatty acid esters and polyoxyethylene castor oil derivatives; polyvinyl alcohol (hereinafter referred to as "PVAs"); polyvinyl pyrrolidone; copolymers of vinyl pyrrolidone and vinyl acetate; copolymers of vinyl pyrrolidone and vinyl caprolactam; carboxycellulose; lecithin; and gelatin; and mixtures thereof. For formation of a stable O/W-type emulsion, PVA, carboxycellulose and gelatin are preferred.

The amount of the emulsifier in the aqueous layer varies depending on the composition ratio of the block copolymer to be granulated, and the concentration is preferably 0.01 to 80% by weight, more preferably 0.05 to 60% by weight, still more preferably 0.1 to 40% by weight for appropriately controlling the particle shape, particle diameter and the like.

To more precisely control the particle shape, particle diameter and the like, a water-soluble organic solvent, in addition to the emulsifier, may be added to the aqueous layer. Examples of such a water-soluble organic solvent include methanol, ethanol, 1-propanol, 2-propanol, 1-butanol, 2-butanol, tert-butyl alcohol, acetonitrile, ethylene glycol, propylene glycol, glycerin, acetone, methyl ethyl ketone, tetrahydrofuran, dimethyl sulfoxide, dimethylformamide and dimethylacetamide. Methanol, ethanol and acetone are preferred, and methanol and ethanol are more preferred since these are highly volatile and less likely to remain in the obtained particle.

The concentration of the water-soluble organic solvent in the aqueous layer is preferably 0.1 to 80% by weight, more preferably 1 to 70% by weight to keep the balance of hydrophobicity/hydrophilicity of the aqueous layer. Further, in consideration of also the production stability, the concentration is preferably 5 to 60% by weight, more preferably 10 to 50% by weight.

The biodegradable particle obtained by droplet solidification granulation in the granulation step is a particle which is generally spherical, that is, spherical particle, but the particle diameter has variation, and in some cases, particles having other shapes may be contained. Therefore, as required, particles having a desired particle shape or particle diameter may be selected from the biodegradable particles obtained in the granulation step. Examples of the method for such selection include sieving. In the sieving, the dispersion medium for dispersing the biodegradable particles is preferably an organic solvent that does not cause dissolution or swelling of the biodegradable particles therein, or water. The dispersion medium is more preferably water.

The biodegradable particles obtained in the granulation step may be subjected to a coating step as required, to prevent aggregation of the biodegradable particles. The coating step herein means a step wherein the surface of the biodegradable particles obtained in the granulation step is covered with a hydrophilic polymer. The coating means a state where the hydrophilic polymer is attached to or adsorbed on the surface of the biodegradable particles. Examples of the method of coating the surface of the biodegradable particles with the hydrophilic polymer include mechanical coating, wet coating, spray drying, sugar coating and powder coating. Among these, wet coating is preferred. In particular, a method wherein biodegradable particles are immersed in a stirred hydrophilic-polymer solution is more preferred.

Examples of the hydrophilic polymer in the coating step include biodegradable materials such as polyalkylene glycols including PEG and polypropylene glycol, and derivatives thereof; polyhydroxyethylmethacrylate; acrylic acid; methacrylic acid; polyvinyl pyrrolidone; copolymers of vinyl pyrrolidone and vinyl acetate; and copolymers of vinyl pyrrolidone and vinyl caprolactam. The hydrophilic polymer is preferably polyalkylene glycol or a derivative thereof, and is more preferably PEG since it has high biocompatibility.

Examples of the solvent to obtain a hydrophilic polymer solution wherein a hydrophilic polymer is uniformly dissolved include water, alcohol-based organic solvents such as methanol, ketone-based organic solvents such as acetone, and halogen-based organic solvents such as dichloromethane and chloroform. Water is preferred since it is inexpensive and highly safe. The concentration of the hydrophilic polymer in the hydrophilic polymer solution varies depending on the type of the biodegradable particle and the like, and is preferably 0.1 to 50% by weight, more preferably 1 to 10% by weight.

The biodegradable particle obtained in the granulation step, or the biodegradable particle obtained in the granulation step and then subjected to the coating step, may be subjected to a drying step if necessary. The drying step herein means a step wherein a liquid such as water contained in the biodegradable particle obtained in the granulation step or the like is removed. The method of removing a liquid such as water include spray drying; convection heat transfer drying such as flash drying and fluidized bed drying; conduction heat transfer drying such as vacuum drying and rotary drum drying; radiation heat transfer drying; microwave drying; and supercritical drying. Conduction heat transfer drying is preferred because of its simplicity.

The "radiation irradiation step" is a step wherein the biodegradable particle obtained in the granulation step, or the biodegradable particle obtained in the granulation step and then subjected to the coating step and/or the drying step, is irradiated with radiation to obtain a sterilized biodegradable particle. Examples of the radiation to be irradiated include α-ray, β-ray, γ-ray, X-ray, ultraviolet and electron beam. In cases where the radiation dose is too low, sterilization may be insufficient, while in cases where the radiation dose is too high, high-energy irradiation may cause over-cross-linking or breakdown of the block copolymer, leading not only to a change in the molecular weight, but also to a too high or too low glass transition point. To provide appropriate flexibility and particle shape-recovering ability to the biodegradable particle obtained in the granulation step, the dose of the radiation irradiated is preferably 5 to 100 kGy, more preferably 10 to 50 kGy, still more preferably 20 to 35 kGy.

EXAMPLES

Our particles, materials and methods are described below in detail by way of Examples and Comparative Examples, but this disclosure is not limited thereto.

Example 1

In an eggplant type flask, 75.0 g of lactide (PURASORB L, manufactured by PURAC) as hydroxycarboxylic acid a1 and 75.0 g of ε-caprolactone (manufactured by Wako Pure Chemical industries, Ltd.) as hydroxycarboxylic acid a2 were placed. These were melt-mixed under nitrogen atmosphere at 120° C., and 0.34 g of tin(II) octylate (manufactured by Sigma Aldrich) as a catalyst was added to the resulting mixture, followed by allowing copolymerization to proceed at normal pressure for 4 hours, to obtain unpurified biodegradable copolymer 1. The glass transition point of a homopolymer produced by homopolymerization of lactide as hydroxycarboxylic acid a1 is 58° C., and the glass transition point of a homopolymer produced by homopolymerization of ε-caprolactone as hydroxycarboxylic acid a2 is −61° C.

In an eggplant type flask, 8.0 g of unpurified biodegradable copolymer 1, 4.0 g of PEG (SUNBRIGHT (registered trademark) DKH-20T, manufactured by NOF Corporation; average molecular weight, 20000) as a water-soluble polymer having a hydroxyl group at both ends, 0.046 g of dodecanedioic acid (manufactured by Wako Pure Chemical Industries, Ltd.) as a polyvalent compound having 2 or more carboxylic acid groups, 0.013 g of tin oxide (manufactured by Wako Pure Chemical industries, Ltd.) as a catalyst, and 12 mL of diphenyl ether (manufactured by Wako Pure Chemical industries, Ltd.) as a solvent were placed. These were melt-mixed at 180° C. and copolymerization reaction was then allowed to proceed at 4 kPa for 20 hours, to obtain raw block copolymer 1.

The obtained raw block copolymer 1 was dissolved in 40 mL of chloroform, and the resulting solution was added dropwise to 640 mL of stirred diethyl ether/hexane=1/1 (weight ratio), to obtain a precipitate, that is, purified block copolymer 1.

The obtained purified block copolymer 1 was dried under reduced pressure and dissolved in dichloromethane to a concentration of 5% by weight, and the resulting solution was collected in a syringe having a 14-G injection needle. On the other hand, 2.8 g of PVA, 120.0 g of methanol and 277.2 g of distilled water were mixed together to prepare 400 mL of aqueous (PVA/methanol) solution containing 0.7% by weight PVA (Sigma Aldrich Japan; average molecular weight, 9000 to 10000) and 30% by weight methanol. To the aqueous (PVA/methanol) solution stirred at a rate of 1.3 $s^{-1}$ at 5° C., the purified block copolymer solution collected in the syringe having an injection needle was added dropwise at a flow rate of 1 mL/min. After completion of the dropwise addition, the stirring rate was changed to 1.7 $s^{-1}$, and stirring was continued at a temperature of not more than 25° C. for 21 hours, followed by carrying out O/W type drying-in-liquid, to obtain spherical biodegradable particles.

The obtained spherical biodegradable particles were selected by sieving, to obtain biodegradable particles having an average particle diameter of 550 μm. More specifically, biodegradable particles that could pass through a sieve having a mesh size of 600 μm, but could not pass through a sieve having a mesh size of 500 μm were collected. Further, spherical particles that could pass through a sieve having a mesh size of 500 μm but could not pass through a sieve having a mesh size of 350 μm were collected to obtain biodegradable particles having an average particle diameter of 400 μm.

A 0.3-g aliquot of each of the selected biodegradable particles having an average particle diameter of 550 μm and biodegradable particles having an average particle diameter of 300 μm was immersed in 200 mL of 5% by weight aqueous PEG (SUNBRIGHT (registered trademark) DKH-10H, manufactured by NOF Corporation; average molecular weight, 1000) solution for 30 hours, and dried at 25° C. for 24 hours, to obtain biodegradable particles having a surface coated with a hydrophilic polymer.

To each of the biodegradable particles with an average particle diameter of 550 μm and biodegradable particles with an average particle diameter of 400 μm having a surface coated with a hydrophilic polymer, γ-ray from cobalt 60 was irradiated such that the minimum dose was 25 kGy, to obtain sterilized biodegradable particles 1 having the respective average particle diameters.

The biodegradable particles 1 having an average particle diameter of 550 μm were dissolved in chloroform and passed through a 0.2-μm syringe filter (Puradisc 13 mm Syringe Filters; manufactured by Whatman) to remove impurities, followed by measurement by the GPC method to calculate the weight average molecular weight of the biodegradable particles 1. The results are shown in Table 2.

The sterilized biodegradable particles 1 having an average particle diameter of 550 μm were dissolved in deuterated chloroform and subjected to measurement by $^1$H-NMR, to calculate each weight ratio in the biodegradable particles 1. The results are shown in Table 2.

Whether or not a dispersion prepared by dispersing 200 mg of the sterilized biodegradable particles 1 (average particle diameter, 550 μm) in 2 mL of an injection solution can be smoothly injected from a syringe to a microcatheter (RENEGADE, manufactured by Boston Scientific; total length, about 1500 mm; inner diameter at the tip, 530 μm) was investigated. Further, visual observation was carried out to investigate whether or not the biodegradable particles 1 were attaching to the inner wall of the syringe after the injection and whether or not the biodegradable particles 1 were remaining on the inner surface of the microcatheter incised longitudinally after the injection. Further, visual observation was also carried out to investigate deformation and disintegration of the biodegradable particles 1 before and after their passing through a catheter.

The sterilized biodegradable particles 1 having an average particle size of 400 μm were placed in the water-saturated state, and the 40% compression load and the compression recovery rate at a compression rate of 10% were measured. The results are shown in Table 2.

As shown in Table 2, the biodegradable particle 1 had a low 40% compression load and a high compression recovery rate at a compression rate of 10%. Further, the biodegradable particle 1 had a good ability to pass through a catheter.

Example 2

The same operations as in Example 1 were carried out except that the weight of lactide was changed to 37.5 g and the weight of ε-caprolactone was changed to 112.5 g, to obtain unpurified biodegradable copolymer 2.

The same operations as in Example 1 were carried out except that unpurified biodegradable copolymer 2 was used instead of unpurified biodegradable copolymer 1, to obtain purified block copolymer 2. Further, the same operations as in Example 1 were carried out for purified block copolymer 2, to obtain sterilized biodegradable particle 2 having the respective particle diameters. These purified block copolymer 2 and biodegradable particle 2 were evaluated in the same manner as in Example 1. The results are shown in Table 2.

As shown in Table 2, biodegradable particle 2 had a low 40% compression load and a high compression recovery rate at a compression rate of 10%. Further, biodegradable particle 2 had a good ability to pass through a catheter.

Example 3

The same operations as in Example 1 were carried out except that the weight of lactide was changed to 25.0 g and the weight of ε-caprolactone was changed to 125.0 g, to obtain unpurified biodegradable copolymer 3.

The same operations as in Example 1 were carried out except that unpurified biodegradable copolymer 3 was used instead of unpurified biodegradable copolymer 1, to obtain purified block copolymer 3. Further, the same operations as in Example 1 were carried out for purified block copolymer 3, to obtain sterilized biodegradable particle 3 having the respective particle diameters. These purified block copolymer 3 and biodegradable particle 3 were evaluated in the same manner as in Example 1. The results are shown in Table 2.

As shown in Table 2, biodegradable particle 3 had a low 40% compression load and a high compression recovery rate at a compression rate of 10%. Further, biodegradable particle 3 had a good ability to pass through a catheter.

Example 4

The same operations as in Example 1 were carried out except that 9.0 g of unpurified biodegradable copolymer 2 was used instead of 8.0 g of unpurified biodegradable copolymer 1, the weight of PEG was changed to 3.0 g, and the weight of dodecanedioic acid was changed to 0.035 g, to obtain purified block copolymer 4. Further, the same operations as in Example 1 were carried out for purified block copolymer 4, to obtain sterilized biodegradable particle 4 having the respective particle diameters. These purified block copolymer 4 and biodegradable particle 4 were evaluated in the same manner as in Example 1. The results are shown in Table 2.

As shown in Table 2, biodegradable particle 4 had a low 40% compression load and a high compression recovery rate at a compression rate of 10%. Further, biodegradable particle 4 had a good ability to pass through a catheter.

Example 5

The same operations as in Example 1 were carried out except that the weight of lactide was changed to 37.5 g, the weight of ε-caprolactone was changed to 112.5 g, and copolymerization was carried out at normal pressure for 16 hours, to obtain unpurified biodegradable copolymer 5.

The same operations as in Example 1 were carried out except that 9.0 g of unpurified biodegradable copolymer 5 was used instead of 8.0 g of unpurified biodegradable copolymer 1, the weight of PEG was changed to 3.0 g, and the weight of dodecanedioic acid was changed to 0.035 g, to obtain purified block copolymer 5. Further, the same operations as in Example 1 were carried out for purified block copolymer 5, to obtain sterilized biodegradable particle 5 having the respective particle diameters. These purified block copolymer 5 and biodegradable particle 5 were evaluated in the same manner as in Example 1. The results are shown in Table 2.

As shown in Table 2, biodegradable particle 5 had a low 40% compression load and a high compression recovery rate at a compression rate of 10%. Further, biodegradable particle 5 had a good ability to pass through a catheter.

Example 6

The same operations as in Example 1 were carried out except that the weight of lactide was changed to 30.0 g, the weight of ε-caprolactone was changed to 90.0 g, and 30.0 g of glycoside (PURASORB G, manufactured by PURAC) as monomer a3 was added, to obtain unpurified biodegradable copolymer 6. The glass transition point of a homopolymer produced by homopolymerization of glycoside as monomer a3 is 36° C.

The same operations as in Example 1 were carried out except that 9.0 g of unpurified biodegradable copolymer 6 was used instead of 8.0 g of unpurified biodegradable copolymer 1, the weight of PEG was changed to 3.0 g, and the weight of dodecanedioic acid was changed to 0.035 g, to obtain purified block copolymer 6. Further, the same operations as in Example 1 were carried out for purified block copolymer 6, to obtain sterilized biodegradable particle 6 having the respective particle diameters. These purified block copolymer 3 and biodegradable particle 6 were evaluated in the same manner as in Example 1. The results are shown in Table 2.

As shown in Table 2, biodegradable particle 6 had a low 40% compression load and a high compression recovery rate at a compression rate of 10%. Further, biodegradable particle 6 had a good ability to pass through a catheter.

Example 7

The same operations as in Example 1 were carried out except that 0.059 g of octacarboxylic acid was used instead of 0.046 g of dodecanedioic acid, 9.0 g of unpurified biodegradable copolymer 2 was used instead of 8.0 g of unpurified biodegradable copolymer 1, and the weight of PEG was changed to 3.0 g, to obtain purified block copolymer 7. Further, the same operations as in Example 1 were carried out for purified block copolymer 7, to obtain sterilized biodegradable particle 7 having the respective particle diameters. These purified block copolymer 7 and biodegradable particle 7 were evaluated in the same manner as in Example 1. The results are shown in Table 2.

As shown in Table 2, biodegradable particle 7 had a low 40% compression load and a high compression recovery rate at a compression rate of 10%. Further, biodegradable particle 7 had a good ability to pass through a catheter.

Comparative Example 1

In an eggplant type flask, 30.0 g of lactide as hydroxycarboxylic acid a1 was placed alone, and heated under nitrogen atmosphere at 160° C., followed by allowing polymerization reaction to proceed according to the pressurization program shown in Table 1 for 4 hours, to obtain unpurified biodegradable copolymer W.

TABLE 1

| | Time [min] | | | | |
|---|---|---|---|---|---|
| | 0 to 20 | 20 to 40 | 40 to 60 | 60 to 120 | 120 to 240 |
| Pressure [kPa] | 50 | 34 | 17 | 4.6 | 1.0 |

The same operations as in Example 1 were carried out except that unpurified biodegradable copolymer W was used instead of unpurified biodegradable copolymer 1, to obtain purified block copolymer W. Further, the same operations as in Example 1 were carried out for purified block copolymer W, to obtain sterilized biodegradable particle W having the respective particle diameters. These purified block copolymer W and biodegradable particle W were evaluated in the same manner as in Example 1. The results are shown in Table 2.

As shown in Table 2, biodegradable particle W had a high 40% compression load and a low compression recovery rate at a compression rate of 10%. Due to insufficient flexibility, the ability of biodegradable particle W to pass through a catheter was not good. After the particle passed through a catheter, its spherical shape could not be maintained, and deformation occurred.

Comparative Example 2

The same operations as in Example 1 were carried out except that ε-caprolactone was used instead of unpurified biodegradable copolymer 1, to obtain purified block copolymer X. Further, the same operations as in Example 1 were carried out for purified block copolymer X, to obtain sterilized biodegradable particle X having the respective particle diameters. These purified block copolymer X and biodegradable particle X were evaluated in the same manner as in Example 1. The results are shown in Table 2.

As shown in Table 2, although biodegradable particle X had a high compression recovery rate at a compression rate of 10%, the 40% compression load exceeded 500 mN. Therefore, the ability of biodegradable particle X to pass through a catheter was not good. Further, since biodegradable particle X had too much flexibility, biodegradable particle X could not maintain its spherical shape after passing through a catheter, and deformation occurred.

Comparative Example 3

The same operations as in Example 1 were carried out except that the weight of lactide was changed to 112.5 g and the weight of ε-caprolactone was changed to 37.5 g, to obtain unpurified biodegradable copolymer Y.

The same operations as in Example 1 were carried out except that unpurified biodegradable copolymer Y was used instead of unpurified biodegradable copolymer 1, to obtain purified block copolymer Y. Further, the same operations as in Example 1 were carried out for purified block copolymer Y, to obtain sterilized biodegradable particles having the respective particle diameters. These purified block copolymer Y and biodegradable particle Y were evaluated in the same manner as in Example 1. The results are shown in Table 2.

As shown in Table 2, biodegradable particle Y had a high 40% compression load and a low compression recovery rate at a compression rate of 10%. Further, due to insufficient flexibility, the ability of biodegradable particle Y to pass through a catheter was not good. After biodegradable particle Y passed through a catheter, its spherical shape could not be maintained, and deformation occurred Comparative Example 4

The same operations as in Example 1 were carried out except that 3-hydroxybutyric acid was used instead of r-caprolactone and the weight of lactide was changed to 37.5 g, to obtain unpurified block copolymer Z. The glass transition point of a homopolymer produced by homopolymerization of 3-hydroxybutyric acid as hydroxycarboxylic acid a2 is 15° C.

The same operations as in Example 1 were carried out except that unpurified biodegradable copolymer Z was used instead of unpurified biodegradable copolymer 1, to obtain purified block copolymer Z. Further, the same operations as in Example 1 were carried out for purified block copolymer Z, to obtain sterilized biodegradable particle Z having the respective particle diameters. These purified block copolymer Z and biodegradable particle Z were evaluated in the same manner as in Example 1. The results are shown in Table 2.

As shown in Table 2, biodegradable particle Z had a high 40% compression load and a low compression recovery rate at a compression rate of 10%. Further, due to insufficient flexibility, the ability of biodegradable particle Z to pass through a catheter was not good. After biodegradable particle Z passed through a catheter, its spherical shape could not be maintained, and deformation occurred

TABLE 2

| Biodegradable particle | Weight average molecular weight | Weight ratio [% by weight] | | | | Compression load [mN] | Compression recovery rate [%] |
|---|---|---|---|---|---|---|---|
| | | A/B | a1/A | a2/A | a3/A | | |
| Example 1 | 55000 | 175 | 50 | 50 | — | 250 | 42 |
| Example 2 | 44000 | 182 | 25 | 75 | — | 445 | 43 |
| Example 3 | 42000 | 170 | 15 | 85 | — | 150 | 51 |
| Example 4 | 86000 | 264 | 23 | 77 | — | 278 | 65 |
| Example 5 | 122000 | 266 | 24 | 76 | — | 139 | 55 |
| Example 6 | 72000 | 260 | 20 | 61 | 19 | 410 | 42 |
| Example 7 | 55000 | 269 | 25 | 75 | — | 117 | 43 |
| Comparative Example 1 | 30000 | 128 | 100 | — | — | 761 | 8 |
| Comparative Example 2 | 28000 | 110 | — | 100 | — | 510 | 52 |
| Comparative Example 3 | 66000 | 179 | 75 | 25 | — | 619 | 36 |
| Comparative Example 4 | 56000 | 181 | 26 | 74 | — | 550 | 21 |

A/B: The weight ratio of block A (a block composed of a copolymer wherein a biodegradable copolymer(s) is/are covalently linked) to block B (a block composed of a water-soluble polymer) in the biodegradable particle (multiblock copolymer)
1/A: The weight ratio of the structure composed of hydroxycarboxylic acid a1 in block A
2/A: The weight ratio of the structure composed of hydroxycarboxylic acid a2 in block A
a3/A: The weight ratio of the structure composed of monomer a3 in block A

INDUSTRIAL APPLICABILITY

The biodegradable particle can be used in the field of medicine to embolize blood vessels.

The invention claimed is:

1. A biodegradable particle comprising a block copolymer produced by copolymerization of:
   a biodegradable copolymer having a structure composed of hydroxycarboxylic acid a1, whose homopolymer produced by homopolymerization has a glass transition point of not less than 40° C., and hydroxycarboxylic acid a2, whose homopolymer produced by homopolymerization has a glass transition point of not more than −40° C.;
   a water-soluble polymer comprising a functional group selected from the group consisting of a hydroxyl group, amino group and carboxylic acid group at each of both ends; and
   a polyvalent compound comprising 2 or more functional groups each selected from the group consisting of a hydroxyl group, amino group and carboxylic acid group; wherein a ratio of mass of said structure composed of hydroxycarboxylic acid a2 to mass of said biodegradable copolymer is 30 to 90% by mass.

2. The biodegradable particle according to claim 1, wherein said block copolymer is a multiblock copolymer comprising a repetitive unit represented by Formula (I) below:

(I)

wherein A represents a block composed of said biodegradable copolymer or a copolymer produced by covalent bonding of 2 or more of said biodegradable copolymer; B represents a block composed of said water-soluble polymer; C represents a single bond or a structure composed of said polyvalent compound; and n represents an integer of 1 or more.

3. The biodegradable particle according to claim 1, wherein a 40% compression load in a water-saturated state is not more than 500 mN and, when a compression rate in the water-saturated state is 10%, compression recovery rate is not less than 40%.

4. The biodegradable particle according to claim 1, wherein weight average molecular weight of said block copolymer is 3000 to 300000.

5. The biodegradable particle according to claim 1, wherein weight average molecular weight of said water-soluble polymer is 200 to 50000.

6. The biodegradable particle according to claim 1, wherein said hydroxycarboxylic acid a1 is lactic acid.

7. The biodegradable particle according to claim 1, wherein said hydroxycarboxylic acid a2 is 6-hydroxycaproic acid.

8. A vascular embolization material composed of the biodegradable particle according to claim 1.

9. A method of producing a sterilized biodegradable particle comprising:
   a copolymerization step of copolymerizing:
     a biodegradable copolymer having a structure composed of hydroxycarboxylic acid a1, whose homopolymer produced by homopolymerization has a glass transition point of not less than 40° C., and hydroxycarboxylic acid a2, whose homopolymer produced by homopolymerization has a glass transition point of not more than −40° C., wherein a ratio of mass of said structure composed of hydroxycarboxylic acid a2 to mass of said biodegradable copolymer is 30 to 90% by mass;
     a water-soluble polymer comprising a functional group selected from the group consisting of a hydroxyl group, amino group and carboxylic acid group at each of both ends; and
     a polyvalent compound comprising 2 or more functional groups each selected from the group consisting of a hydroxyl group, amino group and carboxylic acid to obtain a block copolymer;
   a granulation step of granulating said block copolymer to obtain a biodegradable particle; and
   a radiation irradiation step of irradiating said biodegradable particle with radiation to obtain a sterilized biodegradable particle.

* * * * *